United States Patent
Arkles et al.

(10) Patent No.: US 8,779,080 B2
(45) Date of Patent: Jul. 15, 2014

(54) SILICON COMPOUNDS DERIVED FROM FURFURYL ALCOHOLS AND METHODS OF PREPARATION

(71) Applicant: Gelest Technologies, Inc., Morrisville, PA (US)

(72) Inventors: Barry C. Arkles, Pipersville, PA (US); Youlin Pan, Langhorne, PA (US); Jonathan D. Goff, Philadelphia, PA (US)

(73) Assignee: Gelest Technologies, Inc., Morrisville, PA (US)

( * ) Notice: Subject to any disclaimer, the term of this patent is extended or adjusted under 35 U.S.C. 154(b) by 0 days.

(21) Appl. No.: 14/053,140

(22) Filed: Oct. 14, 2013

(65) Prior Publication Data

US 2014/0046017 A1 Feb. 13, 2014

Related U.S. Application Data

(62) Division of application No. 13/407,820, filed on Feb. 29, 2012.

(60) Provisional application No. 61/449,322, filed on Mar. 4, 2011.

(51) Int. Cl.
| | | |
|---|---|---|
| *C08G 77/14* | (2006.01) | |
| *C07F 7/08* | (2006.01) | |
| *C07F 7/10* | (2006.01) | |
| *C07F 7/18* | (2006.01) | |
| *C08G 77/38* | (2006.01) | |
| *C08G 77/12* | (2006.01) | |

(52) U.S. Cl.
CPC ............. *C07F 7/0852* (2013.01); *C08G 77/12* (2013.01); *C08G 77/14* (2013.01); *C07F 7/184* (2013.01); *C08G 77/38* (2013.01); *C07F 7/1836* (2013.01); *C07F 7/10* (2013.01)
USPC ................. 528/27; 525/477; 528/10; 528/32; 549/214

(58) Field of Classification Search
USPC ..................... 525/477, 479; 549/214; 528/27
See application file for complete search history.

(56) References Cited

U.S. PATENT DOCUMENTS

| | | | |
|---|---|---|---|
| 3,950,364 A | 4/1976 | Vahlensieck et al. | |
| 4,028,384 A | 6/1977 | Vahlensieck et al. | |
| 4,196,131 A | * 4/1980 | Vincent .......................... | 549/214 |
| 4,888,337 A | 12/1989 | Godfroid et al. | |

FOREIGN PATENT DOCUMENTS

JP 04284939 A * 10/1992 ................ B22C 1/16

OTHER PUBLICATIONS

Burger et al, "Silicon in Polymer Synthesis," ed. Kricheldorf, pub. Springer, p. 138 (1996).
Noshay et al, "Block Copolymers: Overview and Critical Survey," Academic Press, p. 400 (1977).
Kanner et al, "Synthesis and Properties of Siloxane-Polyether Copolymer Surfactants," Industrial & Engineering Chemistry Product Research and Development, vol. 6, No. 2, pp. 88-92 (1967).
Liu et al, "One-pot synthesis of tetrahydrofuran derivatives via a divalent palladium-catalyzed three-component coupling," Tetrahedron Letters, vol. 44, pp. 467-470 (2003).
Plueddemann: "Silane Coupling Agents"; Plenum Press New York; pp. 1-5; (Aug. 1, 1982).
U.S. Office Action issued Jul. 12, 2013 in U.S. Appl. No. 13/407,820.

* cited by examiner

*Primary Examiner* — Randy Gulakowski
*Assistant Examiner* — Christopher M Rodd
(74) *Attorney, Agent, or Firm* — Panitch Schwarze Belisario & Nadel LLP

(57) ABSTRACT

Novel silicon compounds containing a siloxane or silane moiety and at least one moiety derived from a furfuryl alcohol, and methods for their synthesis, are provided. The novel compounds may be used as surface modifying agents, surfactants, defoamers, and as monomers for silicone polymerization.

16 Claims, No Drawings

SILICON COMPOUNDS DERIVED FROM FURFURYL ALCOHOLS AND METHODS OF PREPARATION

CROSS-REFERENCE TO RELATED APPLICATIONS

This application is a divisional of co-pending U.S. patent application Ser. No. 13/407,820, filed Feb. 29, 2012, which claims the benefit of U.S. provisional patent Application No. 61/449,322, filed Mar. 4, 2011, the disclosures of which are incorporated herein by reference.

BACKGROUND OF THE INVENTION

Furfuryl alcohol, having the structure shown below, is an organic compound containing a furan substituted with a hydroxymethyl group. Furfuryl alcohol is commercially derived from corncobs and sugar cane bagasse. Commercially, furfuryl alcohol is used to impregnate wood to provide improved moisture-dimensional stability, hardness, and decay and insect resistance. Furfuryl alcohol is also used commercially to prepare furan resins for use in the metal casting industry.

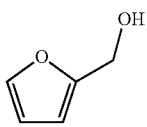

Tetrahydrofurfuryl alcohol, a saturated derivative of furfuryl alcohol, has the following structure:

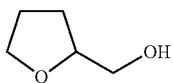

Tetrahydrofurfuryl alcohol is a relatively hydrophilic compound due to the polarity induced by the presence of oxygen atoms and the absence of methyl groups. Tetrahydrofurfuryl alcohol is viewed as relatively non-toxic. The use of tetrahydrofurfuryl alcohol as an adjuvant in synthetic flavoring has been accepted by the FDA (see 21 CFR 172.515), as has the use of tetrahydrofurfuryl alcohol in contact with dry food (see 21 CFR 176.180).

The hydrophilic character of tetrahydrofurfuryl alcohol is in strong contrast to the structures of conventional silicones, such as polydimethylsiloxanes. Polydimethylsiloxanes have many practical uses in which their hydrophobicity provides benefits such as water-repellency and release characteristics. There are many applications in which it is desirable to combine the hydrophobicity of silicones with hydrophilicity. The most widely utilized approach is to modify a polydimethylsiloxane by grafting a poly(ethyleneoxide) segment to the backbone. These materials are often referred to as PEG (from polyethyleneglycol) modified siloxanes. They find applications, for example, as surfactants and antifoams in industrial applications and as emulsifiers for cosmetic formulations. Most of these materials have a minimum of three PEG groups in order to induce satisfactory properties. Less desirable aspects of this chemistry is the fact that they are relatively unstable in aqueous environments due to the oxygen catalyzed break-down of these materials initiated at the carbon atom adjacent to an ethereal oxygen of the PEG. A rupture of a single bond anywhere along the PEG chain renders the materials ineffective, and can cause release of low molecular weight PEGs that suffer from a variety of toxicology issues.

BRIEF SUMMARY OF THE INVENTION

A silicon compound according to the invention comprises a siloxane or silane moiety and at least one furfuryl alcohol-derived moiety.

A method for preparing a silicon compound comprising a siloxane or silane moiety and at least one furfuryl alcohol-derived moiety comprises hydrosilylating a hydride functional silane or siloxane with at least one furfuryl alcohol containing a double bond to yield a hydrolytically stable silicon-to-carbon bond.

DETAILED DESCRIPTION OF THE INVENTION

This invention is directed to siloxane and silicon derivatives of furfuryl alcohols and methods for their preparation. These novel classes of compounds may be used as monomers for surface treatments, as surfactants and defoamers, and for preparing silicone polymers. Due to the greater stability and relatively low toxicity of hydrophilic siloxanes of this invention compared to the PEG modified siloxanes currently used in commerce, these materials provide benefits in varied applications, including cosmetics and medical devices. Depending on the specific siloxane monomers, the resulting silicone polymers may have additional functionality, such as vinyl groups, that allow them to form elastomers in crosslinking processes. The furfuryl substituted siloxanes and silanes are relatively hydrophilic materials and offer the advantage, compared to the most common hydrophilic substituted materials which contain ethylene oxide units, of not degrading to form ethylene glycol or its derivatives. The terahydrofurfuryl siloxanes can also potentially be used as starting points for cationic polymerization of tetrahydrofuran to form block copolymers. For example, linear polydimethylsiloxanes with tetrahydrofuryl groups at the termini could react with tetrahydrofuran by cationic polymerization methods to form ABA, hydroxyl functional (polybutyleneoxide-dimethylsiloxane-polybutyleneoxide triblock polymers.

The siloxane and silane-based compounds according to the invention comprise a siloxane or silane moiety and a moiety derived from a furfuryl alcohol, such as a tetrahydrofurfuryl alcohol in a preferred embodiment. Preferably, the compounds also contain an alkyl bridging group which is bonded to an ether linkage derived from the furfuryl alcohol and to a silicon atom in the siloxane or silane moiety. The alkyl bridge may contain about one to about six carbon atoms. Most preferably, the alkyl bridge contains about three carbon atoms (propyl), which has been found to improve stability of the resulting compound in aqueous environments. Further, propyl-bridged compounds according to the invention are obtainable in higher yield and purity than their shorter alkyl-bridged analogs.

Exemplary silane compounds according to the invention include:

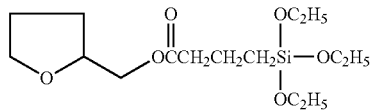

-continued

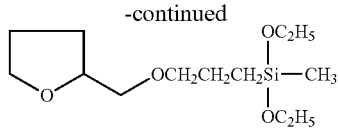

Exemplary siloxane compounds according to the invention include:

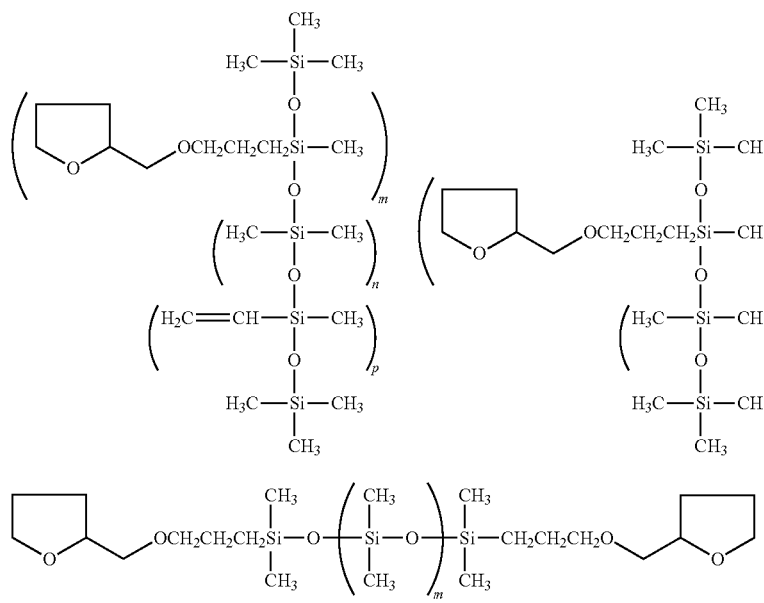

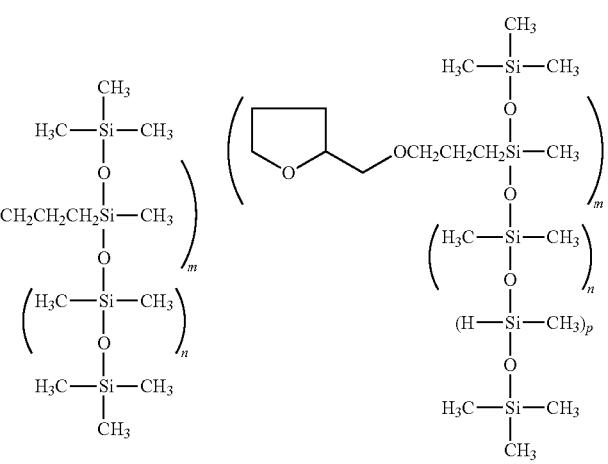

Preferred siloxanes and silanes contain about one to about one thousand silicon atoms, more preferably about one to about eighteen silicon atoms, even more preferably about one to about ten silicon atoms, thus encompassing short chain siloxanes and silanes, which are often referred to as oligosiloxanes and oligosilanes, and longer polysiloxanes and polysilanes. Siloxanes may contain hydrogen and vinyl substituents, and both siloxanes and silanes may contain alkyl or alkoxy substituents (linear or branched, containing up to about eighteen carbon atoms), including methyl substituents, such as polydimethylsiloxanes and oligodimethylsiloxanes, and may also be copolymers, yielding compounds such as (tetrahydrofurfuryloxypropyl)methylsiloxane-dimethylsiloxane copolymers. Terpolymers may also be produced, such as (tetrahydrofurfuryloxypropyl)methylsiloxane-dimethylsiloxane-methylhydrogensiloxane terpolymers and (tetrahydrofurfuryloxypropyl)methylsiloxane-dimethylsiloxane-methylvinylsiloxane terpolymers. Terpolymers of this type may be crosslinked by reaction with each other or by reaction with other vinyl or hydride functional siloxanes in the presence of a hydrosilylation catalyst, for example a platinum catalyst such as Karstedt's catalyst. It is within the scope of the invention for the furfuryl alcohol-derived moiety to occupy a terminal or pendant position on the siloxane or silane, which may have a linear or branched backbone structure.

The invention also includes derivatives in which one silicon-based group is attached to multiple furfuryl alcohol-derived moieties. Thus, silicon compounds containing multiple furfuryl moieties, which may be the same or different, are within the scope of the invention.

Specific preferred compounds according to the invention include, for example, tetrahydrofurfuryloxypropyltriethoxysilane, tetrahydrofurfuryloxypropylheptamethyltrisiloxane, (tetrahydrofurfuryloxymethyl)methyldiethoxysilane, (tetrahydrofurfuryloxypropyl)methylsiloxane-dimethylsiloxane copolymers, and terpolymers including (tetrahydrofurfuryloxypropyl)methylsiloxane-dimethylsiloxane-methylhydrogensiloxane terpolymers and (tetrahydrofurfuryloxypropyl)methylsiloxane-dimethylsiloxane-methylvinylsiloxane terpolymers. Elastomeric and cross-linked products derived from the siloxane polymer, including these copolymer and terpolymers, are also within the scope of the invention.

The compounds according to the invention are shown generally in formula (1):

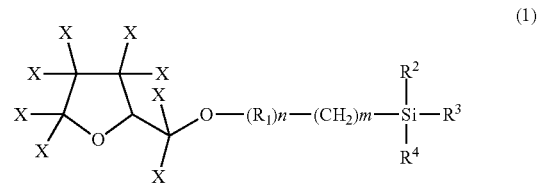

(1)

In formula (1), X, representing the substituents on the tetrahydrofurfuryl alcohol carbons, may be independently hydrogen, methyl, or hydroxyl. Preferably, not more than about two of the X groups are methyl and the compound preferably contains not more than about two hydroxyl substituents. More preferably, all of the X substituents are hydrogen. "n" is an integer selected from 0 and 1, and is preferably 0. $R_1$ represents an optional linkage group, such as carbonyl (C=O) and carbamate (C(O)NH), derived from the reaction of tetrahydrofurfuryl alcohol with an isocyanate functional silane such as isocyanatopropyltriethoxysilane. "m," which represents the length of the alkyl bridge, is an integer from 1 to about 6, preferably about 3. It has been found that propyl linkages between the oxygen atom and the silicon atom are preferred because they yield compounds that are more stable in aqueous environments, and are obtainable in higher yield and purity, than those containing shorter alkyl bridges, such as the silane compound shown below having a methyl bridge (m=1):

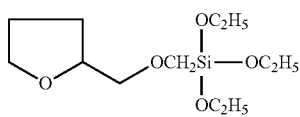

It is also within the scope of the invention to include an ether linkage interrupting the $(CH_2)_m$, for example, (3-tetrahydrofurfuryloxypropoxypropyl)triethoxysilane. In other words, when the compound having formula (1) contains at least three $CH_2$, groups (m≥3), one of the internal $CH_2$ groups may be replaced by oxygen, forming an ether linkage. Another example is:

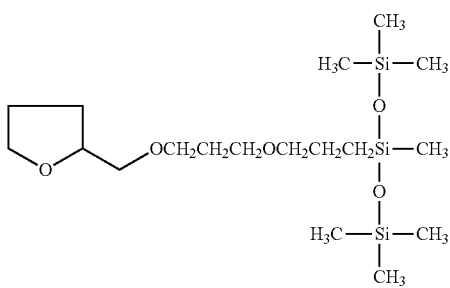

In formula (1), $R^2$, $R^3$, and $R^4$, representing the substituents on silicon, are independently, a substituted or unsubstituted linear or branched alkyl group having about one to four carbon atoms, a substituted or unsubstituted linear or branched alkoxy group having about one to four carbon atoms, or a substituted or unsubstituted siloxy group, provided that at least one of $R^2$, $R^3$, and $R^4$ is an oxygen-containing group (alkoxy or siloxy). Possible substitutions on the siloxy group include hydrogen and vinyl groups, for example. Thus, siloxy groups may have the general formula —$OSiR_3$ or –$OSiR_2$—O—$SiR_3$ (R=alkyl, hydrogen, vinyl, for example. When at least one of $R^2$, $R^3$, and $R^4$ is a siloxy group, the compound having formula (1) is a siloxane compound. Alternatively, the compound is a silane derivative.

As previously explained, it is within the scope of the invention to prepare siloxanes and silanes and siloxanes from substituted derivatives of tetrahydrofurfuryl alcohol.

Preferred compounds according to the invention contain moieties derived from non-substituted furfuryl alcohol, which have the general structure shown in formula (2):

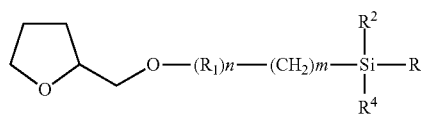

In formula (2), n, m, $R_1$, $R^2$, $R^3$, and $R^4$ have the same definitions as in formula (1).

When $R_1$ is C=O, the compound may considered to be an ester analog, such as the silane compound shown below:

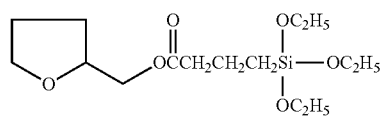

While less stable than their non-ester analogs, such compounds may have sufficient stability in short term exposure to aqueous environments, such as in defoaming or surfactant applications, to offer utility.

Silicon compounds according to the invention may also contain unsaturated derivatives of furfuryl alcohol, such as those having formula (3):

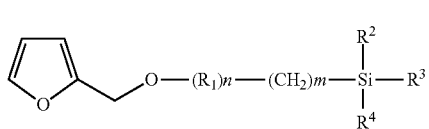

In formula (3), n, m $R_1$, $R^2$, $R^3$, and $R^4$ have the same definitions as in formula (1).

Several different synthetic approaches may be used to prepare the silicon compounds according to the invention. For example, they may be prepared via reaction (hydrosilylation) of a hydride functional silane or siloxane with the appropriate furfuryl alcohol or tetrahydrofurfuryl derivative containing a double bond to yield a hydrolytically stable silicon-to-carbon bond. Such reactions, including appropriate catalysts, solvents, and reaction conditions, are well known in the art.

EXAMPLES

The invention may be further understood in conjunction with the following, non-limiting examples.

Example 1

Preparation of tetrahydrofurfuryloxypropyltriethoxysilane ([2-(3-triethoxysilylpropoxy)methyl]tetrahydrofuran)

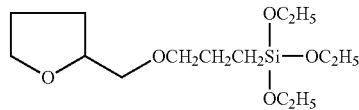

A 1 liter 3 neck flask equipped with a magnetic stirrer, pot thermometer, dry-ice condenser and an addition funnel was charged with 106.6 g of allyloxymethyltetrahydrofuran. The flask was heated to 80° C., and 8.7 g of triethoxysilane was added, followed by 0.5 g of Karstedt's catalyst with a Pt concentration of 2%. An exotherm was observed and an additional 120.6 g of triethoxysilane was added while maintaining the temperature between 80°-100° C. After the addition was complete, an additional 0.25 g of Karstedt's catalyst was added, and the mixture was heated to 90° C. for 1 hour. The mixture was distilled through a short Vigreux column. Tetrahydrofurfuryloxypropyltriethoxysilane (98.7% purity by GC) was obtained in 60% yield, having a boiling point of 130° C./3 mm and a density at 25° C. of 0.9899.

Example 2

Preparation of tetrahydrofurfuryloxypropylheptamethyltrisiloxane

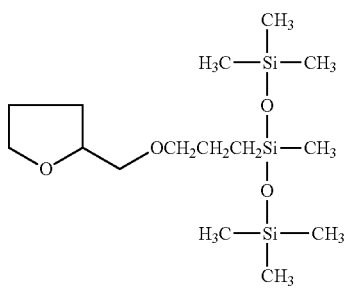

A 1 liter 3 neck flask equipped with a magnetic stirrer, pot thermometer, dry-ice condenser and an addition funnel was charged with 129.3 g of allyloxymethyltetrahydrofuran. The flask was heated to 80° C., and 8.1 g of bis(trimethylsiloxy)methylsilane was added, followed by 0.5 g of Karstedt's catalyst with a Pt concentration of 2%. An exotherm was observed, and an additional 204.5 g of bis(trimethylsiloxy)methylsilane was added, while maintaining the temperature between 80°-110° C. After the addition was complete, an additional 0.25 g of Karstedt's catalyst was added, and the mixture was heated to 90° C. for 1 hour. The mixture was distilled through a short Vigreux column. Tetrahydrofurfuryloxypropylheptamethyltrisiloxane (98.7% purity by GC) was obtained in 84% yield, having a boiling point of 132-6° C./2 mm and a density at 25° C. of 0.9250.

Example 3

Preparation of tetrahydrofurfuryloxymethylheptamethyltrisiloxane

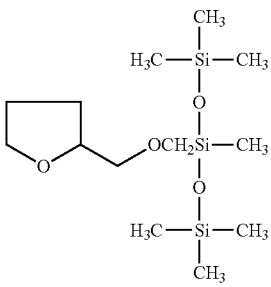

A 2 liter 4 neck flask equipped with a mechanical stirrer, pot thermometer, an addition funnel and a distillation head mounted on a short Vigreux column was charged with ~800 g of heptane and 27.9 g of sodium metal. The flask was heated to 80°-90° C., then 137.9 g of tetrahydrofurfuryl alcohol was added slowly, allowing for hydrogen evolution. The mixture was agitated and heated until all of the sodium was consumed. The flask was allowed to cool to 70° C. and 16.8 g of potassium iodide and 365.8 g of chloromethylheptamethyltrisiloxane were added. The mixture was heated to reflux for 8 hours. Gas chromatography—mass spectral analysis indicated 20% conversion to the desired product. Approximately 250 g of dimethylformamide was added to the mixture and 750 ml of heptane were removed by distillation. The mixture was heated to 90°-100° C. for 8 hours. Conversion to product increased to 40%, but was accompanied by significant byproduct formation.

Example 4

Preparation of (tetrahydrofurfuryloxymethyl)methyldiethoxysilane

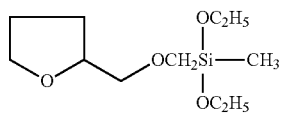

Under conditions similar to Example 3, the reaction product of sodium metal and tetrahydrofurfuryl alcohol was reacted with chloromethylmethyldiethoxysilane in the presence of potassium iodide catalyst in toluene. The reaction proceeded to the desired product only to the extent of 20% with the formation of significant amounts of byproducts.

Example 5

Preparation of 3-(O-tetrahydrofurfurylcarbamoyl)propyltriethoxysilane

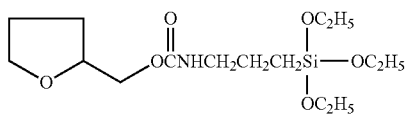

A 2 liter 3 neck flask equipped with a magnetic stirrer, pot thermometer, dry-ice condenser, and an addition funnel was charged with 247.4 g of isocyanatopropyltriethoxysilane and 0.5 g of dibutyltin dilaurate. The flask was heated to 40° C., and 102.1 g of tetrahydrofurfuryl alcohol was added over 50 min at a pot temperature between 40 and 60° C. The pot mixture was heated at 70° C. for another hour after addition was complete. The mixture was stripped at 1 mm Hg at a pot temperature of 60° C. for one hour to give 291 g of 3-(O-tetrahydrofurfurylcarbamoyl)propyltriethoxysilane, a slightly viscous liquid with a density at 25° C. of 1.053. The structure of the product was confirmed by IR and NMR.

The tetrahydrofurfurylcarbamoyl)propyltriethoxysilane was added to water adjusted to pH 4-5 by the addition of acetic acid to form a stable 5% solution. This demonstrates that the hydrolysis product, (tetrahydrofurfurylcarbamoyl)propylsilanetriol, is hydrophilic.

Example 6

Preparation of (tetrahydrofurfuryloxypropyl)methyl-siloxane-dimethylsiloxane-methylhydrogensiloxane terpolymers

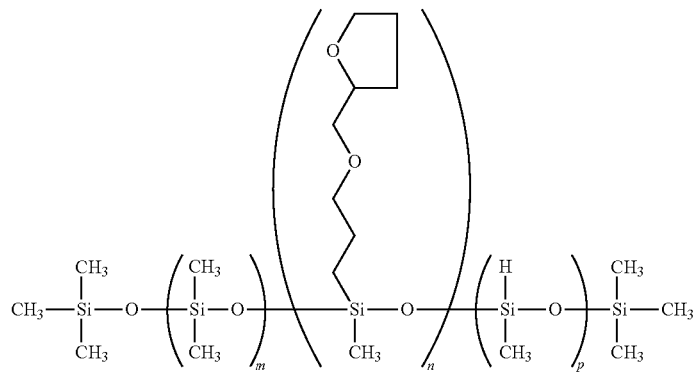

250 g of a 30 mol % methylhydrogensiloxane-70 mole % dimethylsiloxane copolymer was charged to a 1 liter 4-necked round bottom flask equipped with a mechanical stirrer, pot thermometer, addition funnel, and condenser. The reactor was heated to 70° C. under $N_2$ and 0.14 g of Karstedt's catalyst (2.25 wt % Pt in xylene) was charged to the reaction. 73.1 g of tetrahydrofurfuryl allyl ether was added slowly (30 min) via addition funnel to the stirring reaction mixture. An exotherm was observed during addition of the ether, increasing the pot temperature to 80° C. The reaction mixture was allowed to cool to room temperature, yielding a slightly yellow clear liquid with a viscosity of 53 cSt, a density of 1.02 g/cm$^3$ and a refractive index of 1.4223 at 25° C. $^1$H NMR analysis of the recovered copolymer confirmed the quantitative consumption of allyl groups during the hydrosilylation. GPC characterization of the terpolymer showed a $M_n$ of 2300 g mol$^{-1}$ and polydispersity index of 2.5.

Example 7

Synthesis of (30% tetrahydrofurfuryloxypropylmethylsiloxane)-(70% dimethylsiloxane) Copolymer

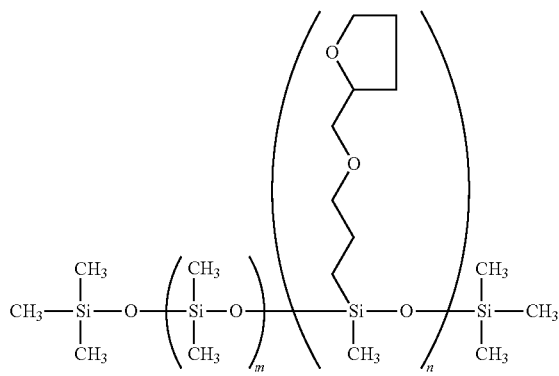

250 g of 30 mol % methylhydrogensiloxane-70 mole % dimethylsiloxane was charged to a 1 liter 4-necked round bottom flask equipped with a mechanical stirrer, pot thermometer, addition funnel, and condenser. The reactor was heated to 70° C. under $N_2$ and 0.14 g of Karstedt's catalyst (2.25 wt % Pt in xylene) was charged to the reaction. 163.2 g of tetrahydrofurfuryl allyl ether was added slowly (1 hr) via addition funnel to the stirring reaction mixture. An exotherm was observed during addition of the ether, increasing the pot temperature to 100° C. Excess tetrahydrofurfuryl allyl ether was removed from the reaction mixture by heating to 110° C. under vacuum (10 mm Hg). The product was allowed to cool to room temperature, yielding 349 g of a slightly brown liquid with a viscosity of 166 cSt, a density of 1.02 g/cm$^3$ and a refractive index of 1.4375 at 25° C. $^1$H NMR and FTIR analysis of the recovered copolymer confirmed the quantitative consumption of hydride groups during the hydrosilylation. GPC characterization of the copolymer showed a $M_n$ of 3000 g mol$^{-1}$ and polydispersity index of 2.6.

Example 8

Elastomeric Reaction of (tetrahydrofurfuryloxypropyl)methylsiloxane-dimethylsiloxane-methylhydrogensiloxane Terpolymers with Vinyl Terminated polydimethylsiloxane 100 g of vinyl terminated polydimethylsiloxane with a viscosity of 1000 cSt was mixed with 0.05 g of Karstedt's catalyst (2.25 wt % Pt in xylene) in a 250 mL beaker. 4.2 g of (15% methylhydrosiloxane)-(15% tetrahydrofurfuryloxypropylmethylsiloxane)-(70% dimethylsiloxane) terpolymer (prepared in Example 6) was charged to the beaker and the two components were thoroughly mixed. The reaction mixture was poured in 20 g aliquots into aluminum pans and heated to 80° C. for 20 minutes, yielding optically clear tetrahydrofurfuryl-modified silicone elastomers.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A silicon compound or siloxane polymer comprising a siloxane moiety and at least one furfuryl alcohol-derived moiety, wherein the silicon compound has formula (1):

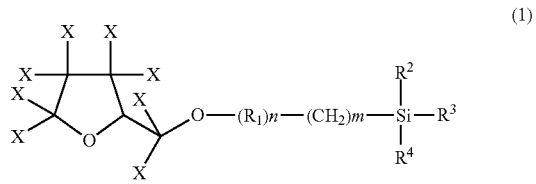

(1)

wherein each X is independently a hydrogen, methyl, or hydroxyl group; n is an integer selected from 0 and 1; $R_1$ is C=O or C(O)NH, m is an integer from one to about six, when m is at least three, one of the internal $CH_2$ groups may be replaced with an oxygen atom, and $R^2$, $R^3$, and $R^4$ are independently a substituted or unsubstituted alkyl group having about one to about four carbon atoms, a substituted or unsubstituted alkoxy group having about one to about four carbon atoms, or a substituted or unsubstituted siloxy group, provided that at least one of $R^2$, $R^3$, and $R^4$ is a siloxy group.

2. The compound according to claim 1, wherein m is three.

3. A silicon compound or siloxane polymer comprising a siloxane moiety and at least one furfuryl alcohol-derived moiety, wherein the furfuryl alcohol is tetrahydrofurfuryl alcohol.

4. The compound according to claim 1, wherein m=3, n=0, and every X=H.

5. The compound according to claim 1, having formula (2):

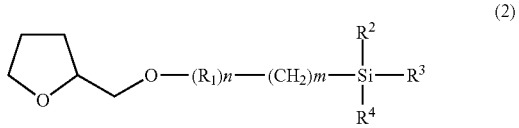

(2)

wherein n is an integer selected from 0 and 1; $R_1$ is C=O or C(O)NH, m is an integer from one to about six, and $R^2$, $R^3$, and $R^4$ are independently a substituted or unsubstituted alkyl group having about one to about four carbon atoms, a substituted or unsubstituted alkoxy group having about one to about four carbon atoms, or a substituted or unsubstituted siloxy group, provided that at least one of $R^2$, $R^3$, and $R^4$ is a siloxy group.

6. The compound according to claim 1, wherein the silicon compound is tetrahydrofurfuryloxypropyl-heptamethyltrisiloxane.

7. A silicon compound or siloxane polymer comprising a siloxane moiety and at least one furfuryl alcohol-derived moiety, wherein the silicon compound has formula (3):

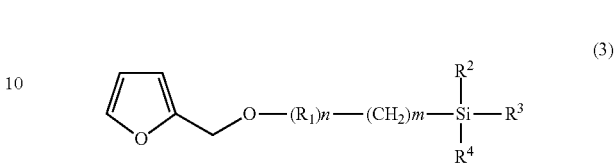

(3)

wherein n is an integer selected from 0 and 1; $R_1$ is C=O or C(O)NH, m is an integer from 1 to about six, and $R^2$, $R^3$, and $R^4$ are independently a substituted or unsubstituted alkyl group having about one to about four carbon atoms, a substituted or unsubstituted alkoxy group having about one to about four carbon atoms, or a substituted or unsubstituted siloxy group, provided that at least one of $R^2$, $R^3$, and $R^4$ is a siloxy group.

8. A surface modifying reagent comprising a silicon compound according to claim 1.

9. A surfactant comprising a silicon compound according to claim 1.

10. A siloxane polymer comprising a siloxane moiety and at least one furfuryl alcohol-derived moiety, wherein the polymer contains a tetrahydrofurfuryloxyalkyl substitution.

11. The compound according to claim 10, wherein the siloxane polymer is a (tetrahydrofurfuryloxypropyl)methylsiloxane-dimethylsiloxane copolymer.

12. The compound according to claim 10, wherein the siloxane polymer is selected from the group consisting of a (tetrahydrofurfuryloxypropyl)methylsiloxane-dimethylsiloxane-methylhydrogensiloxane terpolymer and a (tetrahydrofurfuryloxypropyl)methylsiloxane-dimethylsiloxane-methylvinylsiloxane terpolymer.

13. An elastomeric and cross-linked product derived from at least one terpolymer according to claim 12.

14. The compound according to claim 10, wherein the siloxane polymer is a siloxane homopolymer or copolymer having a hydride or vinyl terminal group.

15. An elastomeric and cross-linked product derived from the copolymer or homopolymer according to claim 14.

16. An elastomeric silane formed by the reaction of the polymer according to claim 14 with a hydride- or vinyl-containing siloxane.

* * * * *